(12) United States Patent
Gemmel et al.

(10) Patent No.: US 10,413,367 B2
(45) Date of Patent: Sep. 17, 2019

(54) METHOD OF PERFORMING INTRAOPERATIVE NAVIGATION

(71) Applicant: SIEMENS HEALTCARE GMBH, Erlangen (DE)

(72) Inventors: Alexander Gemmel, Erlangen (DE); Gerhard Kleinszig, Forchheim (DE); Wei Wei, Forchheim (DE); Markus Weiten, Nuremberg (DE); Christoph Tilgener, Grafenwoehr (DE)

(73) Assignee: Siemens Healthcare GmbH, Erlangen (DE)

( * ) Notice: Subject to any disclaimer, the term of this patent is extended or adjusted under 35 U.S.C. 154(b) by 456 days.

(21) Appl. No.: 15/167,027

(22) Filed: May 27, 2016

(65) Prior Publication Data
US 2017/0340394 A1  Nov. 30, 2017

(51) Int. Cl.
| | | |
|---|---|---|
| *A61B 6/12* | (2006.01) | |
| *A61B 6/02* | (2006.01) | |
| *G06T 19/00* | (2011.01) | |
| *G01R 23/16* | (2006.01) | |
| *A61B 34/20* | (2016.01) | |
| *H04N 5/77* | (2006.01) | |
| *A61B 6/00* | (2006.01) | |
| *A61B 90/00* | (2016.01) | |
| *G06T 7/11* | (2017.01) | |

(52) U.S. Cl.
CPC ........... *A61B 34/20* (2016.02); *A61B 6/12* (2013.01); *A61B 6/4417* (2013.01); *A61B 6/5247* (2013.01); *A61B 90/37* (2016.02); *G06T 7/11* (2017.01); *H04N 5/77* (2013.01); *A61B 90/361* (2016.02); *A61B 2034/2057* (2016.02); *A61B 2034/2065* (2016.02); *A61B 2090/376* (2016.02); *G06T 2207/10116* (2013.01); *G06T 2207/30241* (2013.01)

(58) Field of Classification Search
CPC .................................. A61B 5/05; A61B 31/20
See application file for complete search history.

(56) References Cited

U.S. PATENT DOCUMENTS

| | | | |
|---|---|---|---|
| 2004/0152970 A1* | 8/2004 | Hunter | A61B 17/025 600/424 |
| 2013/0148779 A1* | 6/2013 | Notohara | A61B 6/025 378/22 |
| 2015/0201892 A1* | 7/2015 | Hummel | A61B 6/5229 348/77 |

FOREIGN PATENT DOCUMENTS

| | | |
|---|---|---|
| DE | 102014219436 A1 | 3/2016 |
| WO | 2016046032 A1 | 3/2016 |

* cited by examiner

*Primary Examiner* — Patricia I Young
(74) *Attorney, Agent, or Firm* — Laurence Greenberg; Werner Stemer; Ralph Locher

(57) ABSTRACT

The invention describes a method of performing intraoperative navigation during a surgical procedure, which method comprises the steps of arranging a video imaging device on a radioscopic imaging apparatus; obtaining an initial radioscopic image of a target and identifying a desired trajectory in a target; determining a first position of the radioscopic imaging apparatus relative to the target for which a central image axis of a radioscopic imaging unit is aligned with the desired trajectory; positioning the radioscopic imaging apparatus to align a central image axis of the video imaging device with the desired trajectory; and showing a live video feed of the surgical procedure on a monitor to track the position of a surgical implement relative to the desired trajectory.

21 Claims, 2 Drawing Sheets

METHOD OF PERFORMING INTRAOPERATIVE NAVIGATION

BACKGROUND OF THE INVENTION

Field of the Invention

The invention describes a method of performing intraoperative navigation during a surgical procedure; and a system for performing intraoperative navigation.

For a complex surgical intervention, it can be advantageous to plan a navigated procedure in advance. It can also be helpful to be able to refer to the navigation during the actual surgical intervention. Navigation can provide the surgeon with a level of assistance that goes beyond the conventional operative methods. A navigation system assists in the precise placement of material in or on the patient, and generally comprises an X-ray apparatus for use in a surgical theatre and a video apparatus. The X-ray apparatus comprises a radiation source and a detector that are arranged to fit around an operating table. At some point during the surgical intervention, the X-ray apparatus can be used to generate X-ray images that can be analyzed to monitor the progress of the surgical procedure. Previously, the position and orientation of instruments or material have been determined using conventional navigation systems. Such a prior art navigation system generally comprises an optical or electromagnetic tracking system that can detect or track a marker placed on the patient as a reference and the instruments. The marker assists in the orientation and positioning of an instrument or placement of material in the patient. While the conventional navigation system can visually display the instruments and material to the user, its accuracy depends on how accurately the reference marker is "fixed" relative to the patient. Therefore, such a marker may require an additional incision, or may even be anchored to bone. Placement of the marker itself is therefore invasive. A further problem with such conventional navigation systems is that they generally occupy a relatively large space, and may hamper the workflow in an already crowded operating room. Typically, line of sight problems impair the performance of a conventional navigation system.

In an alternative approach, the navigation can be augmented by a laser marker generated at the conjunction of two angled laser beams, which depict the central X-ray beam axis. During the surgical procedure, the laser marker is projected onto the patient's skin at a target area or region of interest determined in advance by the surgeon. A problem with this approach is that the laser can only indicate a single direction. This means that the imaging and navigation must be performed in the same direction. Furthermore, the laser marker can only be projected onto the region of interest when there is sufficient distance between the patient and the detector. This means that it cannot be used during procedures that require the patient to be close to the detector. Equally, if the laser marker is necessary during a surgical procedure, the X-ray apparatus can only be used to generate images at a larger detector distance. However, the weight of the X-ray apparatus may also lead to a slight distortion and loss of accuracy of a projected laser marker. Another problem is that the navigated direction is shown to the surgeon by the laser marker only, i.e. the surgeon is not given any additional assistance.

BRIEF SUMMARY OF THE INVENTION

It is therefore an object of the invention to provide an improved navigation system that overcomes the problems described above.

This object is achieved by the method as claimed of performing intraoperative navigation during a surgical procedure; and by the system as claimed for performing intraoperative navigation during a surgical procedure.

According to the invention, the method of performing intraoperative navigation during a surgical procedure comprises at least the steps of arranging a video imaging device on a radioscopic imaging apparatus;

obtaining an initial radioscopic image of a target and identifying a desired trajectory in the target;

determining a first position of the radioscopic imaging apparatus relative to the target for which a central image axis of a radioscopic imaging unit is aligned with the desired trajectory; and positioning the radioscopic imaging apparatus to align a central image axis of the video imaging device with the desired trajectory;

showing a live video feed of the surgical procedure on a monitor to track the position of a surgical object relative to the desired trajectory.

In the context of the invention, the desired trajectory is identified on the basis of a radioscopic image of the target. This step can be performed using a suitable interface so that the desired trajectory can be defined as a set of coordinates in a coordinate system of the radioscopic imaging apparatus.

An advantage of the method according to the invention is that the intraoperative navigation is less dependent on the distance between detector and patient. This is in contrast to a conventional laser-based navigation technique, which requires a minimum distance between detector and patient. A further advantage arises from the inventive approach of determining the first position of the radioscopic imaging apparatus from the desired trajectory identified in the initial radioscopic image (this first position would align the central image axis of the radioscopic imaging unit with the desired trajectory); and then positioning the radioscopic imaging apparatus to align a central image axis of the video imaging device with the desired trajectory. This combination of steps is made possible by knowledge of the position of the video imaging device relative to the radioscopic imaging apparatus, as will be explained in more detail below. The video imaging device is then always directed along the desired trajectory. By observing the live video feed during the surgical procedure, the surgeon can therefore always relate a position of an implement as seen on the monitor—e.g. an object to be implanted, a surgical instrument, etc.—to the desired trajectory. The accuracy of the intraoperative navigation can therefore be increased significantly. Since the method of the invention allows the surgical procedure to be carried out without any interruptions related to navigation, it can help in achieving an optimal workflow.

According to the invention, the system for performing intraoperative navigation during a surgical procedure comprises at least a radioscopic imaging apparatus carrying a radioscopic imaging arrangement;

a video imaging device arranged on the radioscopic imaging apparatus at a fixed position relative to the radioscopic imaging unit;

a computation unit adapted to determine a first position of the radioscopic imaging apparatus for which a central image axis of the radioscopic imaging unit is aligned with a desired trajectory previously identified in an initial radioscopic image of the target;

a positioning means adapted to position the radioscopic imaging apparatus to align a central image axis of the video imaging device with the desired trajectory; and a monitor for showing a live video feed to track a surgical object during the surgical procedure.

The inventive system makes use of a known and fixed relationship between the central image axis of the radioscopic imaging unit and the central image axis of the video imaging device to align the video imaging device accurately along the desired trajectory. As explained above, the desired trajectory is determined from an initial radioscopic image of the target and this trajectory can be defined in a coordinate system of the radioscopic imaging arrangement.

An advantage of the inventive system is that the position—relative to the target—of a critical object used during the procedure can be shown to the surgeon in a more accurate manner compared to the conventional navigation techniques, allowing the surgeon more control in manipulating and moving the object.

Particularly advantageous embodiments and features of the invention are given by the dependent claims, as revealed in the following description. Features of different claim categories may be combined as appropriate to give further embodiments not described herein.

In the following, without restricting the invention in any way, it may be assumed that the "target" is a patient undergoing a surgical procedure, and the terms "target" and "patient" may be used interchangeably in the following. From the point of view of the surgeon, the target may be restricted to a certain "region of interest" in the patient's body. The term "surgical object" may refer to a surgical instrument, an implant to be positioned in the patient, or any such surgically related item.

A radioscopic imaging apparatus of the type used to generate images during a surgical procedure is usually an X-ray imaging apparatus, since this kind of device can quickly provide a projection through a defined region in the body of the patient. In the following, it may be assumed that the radioscopic imaging apparatus is an X-ray apparatus.

The radioscopic imaging apparatus of the inventive system may be assumed to be a mobile motorized radiography unit as disclosed in DE 10 2014 219 436 A1, which is incorporated herein by reference. The radioscopic imaging apparatus or "mobile C-arm" comprises a radiation source and a radiation detector arranged at the extremities of a C-shaped arm. The arc-shaped or C-shaped arm is designed to fit about a patient lying on an operating table with the radiation source usually underneath the patient, and the radiation detector usually above the patient. An advantage of the inventive system using the mobile C-arm is that the surgeon is given more room to maneuver, since the C-arm can be tilted to move the X-ray apparatus aside without moving it away completely, and at the same time bringing the video apparatus in line with the desired trajectory.

In the following, the terms "radioscopic imaging apparatus" and "mobile C-arm" may be used interchangeably. Such a mobile C-arm comprises a number of motors and drives for moving the entire C-arm freely in the operating room; for moving the detector inwards or outwards along an image axis relative to the source; and for tilting the C-arm (and therefore also the source and detector). The source and detector are always aligned along a common image axis, which may be referred to in the following as the "detector axis". To precisely control the position of the mobile apparatus, the position of the C-arm, and the position of the detector, these elements or units are equipped with motors and suitable drivers, and the positioning means of the system preferably comprises a position controller that is adapted to generate motion parameters or corresponding control signals required by the driver or drivers required to achieve a desired position of the mobile apparatus and/or the C-arm and/or the detector.

In the inventive system, the video imaging device is preferably arranged on the radioscopic imaging apparatus at a fixed position relative to the detector. Preferably, the video imaging device is arranged on the radioscopic imaging apparatus such that the central image axis of the video imaging device (the "camera axis" in the following) subtends a fixed angle to the detector axis. In other words, the position of the camera axis is defined in the coordinate system of the radioscopic imaging apparatus. The relative positions of the detector axis and camera axis in a coordinate system of the radioscopic imaging apparatus are preferably established to a high degree of precision during an initial calibration step.

Initially, before commencing the surgical procedure, the surgeon can bring the C-arm into position relative to the target to generate an initial X-ray image. As explained above, the surgeon can identify the desired trajectory in this initial X-ray image, which can be generated immediately prior to the surgical procedure. The surgeon can identify the desired trajectory using a suitable graphical user interface of the system. Preferably, the graphical user interface is linked to the position controller of the mobile C-arm apparatus, so that the desired trajectory can be used to generate position parameters for the C-arm and the detector. This information is sufficient to determine a first C-arm position in which the detector image axis coincides with the desired trajectory.

On the basis of this information, the C-arm is subsequently positioned so that the image axis of the camera coincides with the desired trajectory. Motion parameters for re-positioning the C-arm are preferably determined in the computation unit. The positioning step can be performed manually by an operator, following the position parameters supplied by the computation unit. Alternatively, re-positioning is performed in a fully automated manner. The C-arm is now in a position or orientation that allows the camera to record the actions of the surgeon during a critical stage of the surgical procedure. During the surgical procedure, a live video feed is displayed on the monitor. The surgeon knows that the trajectory is perpendicular to the monitor plane, i.e. the image plane of the video feed. This allows the surgeon to accurately place any instrument such as a bone drill, a needle, a screwdriver etc. that must be directed along the trajectory. For example, for a threaded screw implant to be placed correctly, a bone drill must drill along the trajectory, and the screwdriver must be positioned along the same trajectory. In the live video feed, which can "zoom in" to show a magnified view, the surgeon can easily see whether an object is correctly held in alignment with the trajectory.

In a further preferred embodiment of the invention, a visual alignment aid is also shown in the live video feed. For example, a graphical element in the form of a clearly visible dot may be overlaid on the live video feed. A visual alignment aid in this form is preferably centered on a point that corresponds to the intersection of the desired trajectory with the video image plane. This allows the surgeon to correctly position and align an object such as a needle, a screwdriver, an implant, etc. The surgeon can move the object so that it appears to lie exactly "underneath" the dot.

The visual alignment aid can have any other suitable appearance, for example a circle centered on the intersection point of the desired trajectory with the video image plane, or crosshairs, etc.

The form and position of the visual alignment aid in the live video feed can be determined in an image processing unit of the inventive system. Such an image processing unit is preferably adapted to receive video data from the video imaging device, and to receive coordinate information from the system's computation unit. Using suitable software algorithms, the image processing unit can determine a trajectory point in the live video feed that corresponds to an intersection of the desired trajectory with a video image plane, and can overlay a graphical element on the live video feed, as a visual alignment aid to the surgeon.

In a further preferred embodiment of the invention, the image processing unit is adapted to determine a degree of alignment between a surgical implement and the desired trajectory. This can be established by processing one or more images to detect the shape of an instrument or object, to deduce its longitudinal axis, and to compare this with the desired trajectory. Any discrepancy or misalignment could be indicated to the surgeon, for example by overlaying a suitable graphical element over the live video feed.

Further information can be shown in the guidance overlay, for example a discrepancy between the intended instrument position and the actual instrument position. A previously generated 2D X-ray image, for example the initial radioscopic image, can also be virtually included in the guidance overlay.

During a critical surgical procedure, the surgeon may need to verify the accuracy of any object placed in the patient. Therefore, in a further preferred embodiment, the inventive method comprises a step of actuating the radioscopic imaging unit to generate a verification image during the surgical procedure. The verification image is generated without having to interrupt the navigation, since the X-ray apparatus is already in place, with the detector axis at an angle relative to the camera axis. With this setup, an image of the target is taken "from the side". This lateral image will show the material in the patient's body, and the surgeon can assess the image to determine whether the placement is correct, or whether any adjustments should be undertaken. Such a verification image can allow the operator to place an instrument or material more accurately or to confirm the correctness of the procedure up to that point, without having to interrupt the navigation.

The visual alignment aid can improve the accuracy of object placement during a surgical procedure to such an extent that only an initial X-ray image and a verification X-ray image (after conclusion of the procedure) may be required. This can favorably reduce radiation exposure levels for the patient and the operating team.

The steps of image processing, motion parameter computation, radioscopic image processing etc., can be performed in software, as will be known to the skilled person.

Realizing these functions in the form of software has the advantage that existing control units can easily be upgraded by a software update in order to carry out one or more steps of the inventive method. The object of the invention can therefore also be achieved by a suitable computer program product with a computer program that is directly loadable into a memory of a control unit of an intraoperative navigation system and which comprises program elements for performing the steps of the method when the computer program is executed by the computation unit of the intraoperative navigation system. Such a computer program product can—in addition to the computer program—comprise further parts such as documentation, hardware components such as hardware keys (e.g. a dongle) to access the software, etc.

A computer readable medium such as a memory stick, a hard-disk or other storage medium can be used to store the computer program and/or to transfer the computer program to the computation unit of the intraoperative navigation system, which computation unit may avail of one or more microprocessors to execute the computer program.

Other objects and features of the present invention will become apparent from the following detailed descriptions considered in conjunction with the accompanying drawings. It is to be understood, however, that the drawings are designed solely for the purposes of illustration and not as a definition of the limits of the invention.

BRIEF DESCRIPTION OF THE SEVERAL FIGURES OF THE DRAWING

In the diagrams, like numbers refer to like objects throughout. Objects in the diagrams are not necessarily drawn to scale.

DESCRIPTION OF THE INVENTION

Figure 1:
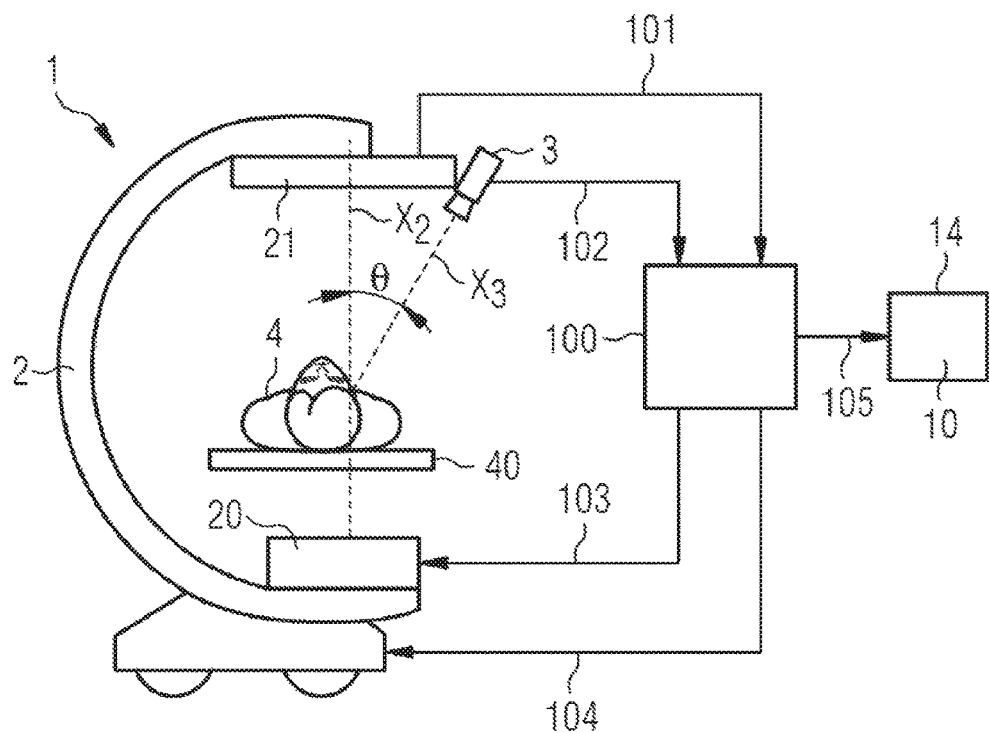
FIG. 1 shows a schematic diagram of the intraoperative navigation system according to the invention in a first orientation.
Figure 2:
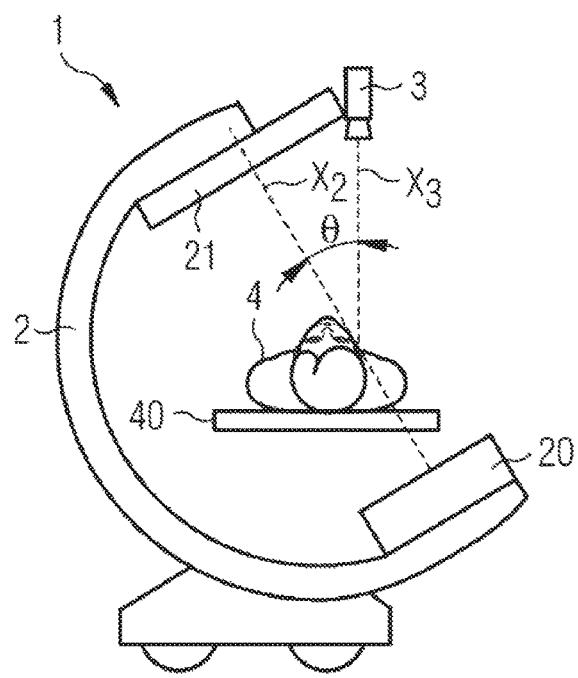
FIG. 2 shows a schematic diagram of the intraoperative navigation system of FIG. 1A in a second orientation.

FIG. 1 and FIG. 2 show a simplified diagram of the intraoperative navigation system 1 according to the invention. The diagrams show a mobile C-arm X-ray apparatus 2 as disclosed in DE 10 2014 219 436 A1. The mobile C-arm 2 or "imaging unit" 2 supports an X-ray source 20 and a detector 21, and can be arranged relative to a patient 4 (on a table 40) so that the X-ray source 20 and detector 21 are on opposite sides of the patient 4. The surgeon can use the mobile C-arm apparatus to obtain an X-ray image prior to and/or during a surgical procedure.

The mobile C-arm 2 comprises various motors and drives (not shown) which can be actuated to move the detector 21 inward or outward from the radiation source 20 according to the desired X-ray image size, and to tilt the C-arm with the detector and X-ray source at a desired angle. In this way, an X-ray image can be obtained from essentially any desired aspect. A computation unit 100 is realized to generate any motion parameters 104 or driver control signals 104 to effect a desired movement of the entire mobile C-arm 2, a tilting of the C-arm 2, or an adjustment of the detector 21 relative to the radiation source 20. This is explained in detail in DE 10 2014 219 436 A1.

The exemplary intraoperative navigation system 1 augments the mobile C-arm X-ray apparatus 2 by a video camera 3 mounted at a fixed position beside the detector 21 on the C-arm so that it can be directed at a region of interest during the surgical procedure. The orientation of the camera main axis $X_3$ relative to the imaging unit main axis $X_2$—indicated by angle θ in the diagrams—is fixed and known. The orientation of the camera 3 relative to the imaging unit 2 can be defined in terms of the coordinate system of the imaging unit 2.

In an exemplary procedure, the surgeon can position the imaging unit 2 relative to the patient 4 to obtain an initial X-ray image showing the region of interest. For example, if the surgical procedure is to be carried out on a vertebra, the initial X-ray image is preferably centered on that vertebra. The surgeon then identifies a desired trajectory. This may be the axis of a threaded implant which is to be screwed into the vertebra. The surgeon can identify the desired trajectory by using a suitable graphical user interface to mark a point along the planned implantation axis. This information is given to the computation unit 100, which then computes any motion parameters 104 that would be required in order to move the imaging unit 2 to bring its central image axis $X_2$ into alignment with the desired trajectory. This orientation is indicated in FIG. 1, and these motion parameters effectively therefore define a "first position" of the imaging unit 2. Knowing this "first position", and knowing the orientation of the camera axis $X_3$ relative to the detector axis $X_2$, it is now possible to position the imaging unit 2 to align the camera axis $X_3$ with the desired trajectory, as shown in FIG. 2. Video data 102 from the camera 3 is sent to the computation unit 100, which comprises any suitable image processing units for presenting a live video feed of the surgical procedure on a monitor 14.

For simplicity, the diagrams show the camera axis $X_3$ (and desired trajectory) as a vertical axis. However it should be understood that the desired trajectory can lie along any line at any angle, depending on the nature of the surgical procedure that is to be carried out. In that case, the mobile C-arm will be tilted accordingly in its "first position", and offset from that first position to bring the camera axis $X_3$ in line with the desired trajectory.

Figure 3:
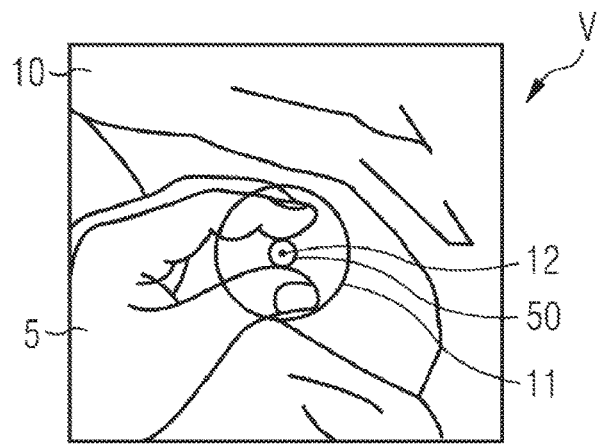
FIG. 3 shows a schematic diagram of a live video feed obtained during a surgical procedure.
Figure 4:
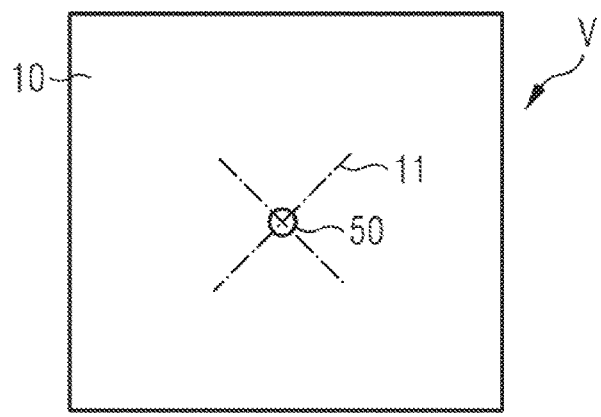
FIG. 4 shows another schematic diagram of a live video feed obtained during a surgical procedure.
Figure 5:
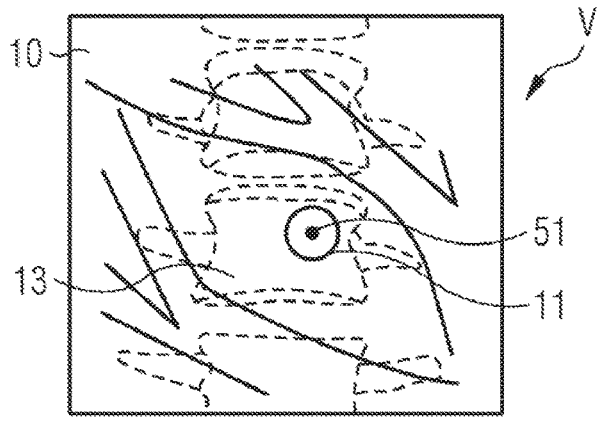
FIG. 5 shows another schematic diagram of a live video feed obtained during a surgical procedure.

The live video feed, shown schematically in FIGS. 3-5, allows the surgeon to track the position of an instrument relative to the desired trajectory. The surgeon, when looking at the centre of the live video feed, can be certain that the camera's "line of sight" coincides with the desired trajectory. To further assist the surgeon, a visual alignment aid or guide overlay can be included in the live video feed. This allows the surgeon to place material such as an implant (a threaded screw in the above example) or instrument (a bone drill, a needle or a screwdriver in the above example) with a high degree of precision, without impeding the surgeon's own line of sight.

FIG. 3 shows a "screenshot" 10 of the live video feed V, obtained during the surgical procedure. The diagram shows a surgical site exposed for the procedure. A guide overlay 11 is centered on a point corresponding to an intersection 12 of the desired trajectory with the video image plane (the plane of the page in the drawing). The diagram shows an instrument 50 being held in the surgeon's hand 5 so that the instrument axis is aligned correctly with the desired trajectory. This is confirmed to the surgeon by the concentric alignment of the instrument 50 within the circular guidance overlay 11. Since the camera axis is aligned with the desired trajectory, the surgeon knows that the centre of the guide overlay 11 coincides with the desired trajectory. The surgeon can use this visual information to precisely align the axis of an object —implant or instrument—with the desired trajectory. Looking at the video feed, the surgeon can see if the object 50 is being held correctly. Any departure from the correct alignment will be immediately evident and can be corrected. The live video feed V can "zoom in" towards the patient if desired by the surgeon, since a magnified video image may allow a more precise positioning of the instrument or material relative to the desired trajectory.

In FIG. 4, the guide overlay G is shown as cross-hairs that intersect at the point corresponding to an intersection of the desired trajectory with the video image plane. The other details shown in FIG. 3 have been left out for simplicity.

FIG. 5 shows a further elaboration of the live video feed. Here, the video feedback V is augmented by an X-ray image 13, in this case a radioscopic image obtained with the C-arm in its first position, i.e. with its detector axis aligned with the trajectory. This X-ray image 13 is overlaid on the live video feed V. The added information may assist the surgeon in assessing the accuracy of the procedure at that stage. In this example, the surgeon inserted a pedicle screw 51 using a screwdriver 50.

To verify correct placement, an X-ray image is made using the imaging unit. This can be done without moving the C-arm, i.e. without interrupting the instrument navigation. The verification image therefore shows the progress of the surgical procedure from the side. Any discrepancy can be immediately corrected by the surgeon before continuing the procedure. Such verification images can be obtained as necessary at any stage during the surgical procedure. However, since the surgeon can align any material very precisely along the desired trajectory using the live video feed and a radioscopic image obtained in the first position of the C-arm, it may be possible to perform the entire surgical procedure on the basis of one or more such initial X-ray images alone, and to obtain a final verification image only upon conclusion of the surgical procedure. In this way, the patient and staff are exposed to only a minimum radiation dose. Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method of performing intraoperative navigation during a surgical procedure, which method comprises the steps of:
   arranging a video imaging device on a radioscopic imaging apparatus being a C-arm, the radioscopic imaging apparatus having a radioscopic imaging unit with a central image axis separate and different from a central image axis of the video imaging device, the central image axis of the radioscopic imaging unit and the central image axis of the video imaging device subtending a fixed angle relative to one another;
   obtaining an initial radioscopic image of a target and identifying a desired trajectory in the target;
   determining a first position of the radioscopic imaging apparatus relative to the target for which the central image axis of the radioscopic imaging unit is aligned with the desired trajectory;
   moving the radioscopic imaging apparatus to align the central image axis of the video imaging device with the desired trajectory; and
   showing a live video feed of the surgical procedure on a monitor and overlaying a radioscopic image in the live video feed to track the position of a surgical object relative to the desired trajectory.

2. The method according to claim 1, wherein the desired trajectory is indicated in the live video feed.

3. The method according to claim 1, comprising a step of overlaying a visual alignment aid in the live video feed.

4. The method according to claim 3, wherein the visual alignment aid is centered on a point corresponding to an intersection of the desired trajectory with a video image plane.

5. The method according to claim 1, wherein the step of identifying the desired trajectory is performed on the basis of the initial radioscopic image of the target by inputting information via a graphical user interface.

6. The method according to claim 1, comprising the steps of bringing the radioscopic imaging apparatus into the first position, generating a radioscopic image, and overlaying the radioscopic image in the live video feed.

7. The method according to claim 1, comprising an initial calibration step to define a position of the video imaging device in a coordinate system of the radioscopic imaging apparatus.

8. A system for performing intraoperative navigation during a surgical procedure, which intraoperative navigation system comprises a radioscopic imaging apparatus being a C-arm comprising a radioscopic imaging arrangement;

a video imaging device arranged on the radioscopic imaging apparatus at a fixed position relative to the radioscopic imaging unit, the video imaging device having a central image axis separate and different from a central image axis of said radioscopic imaging apparatus, and the central image axis of the radioscopic imaging unit and the central image axis of the video imaging device subtending a fixed angle relative to one another;

a computation unit adapted to determine a first position of the radioscopic imaging apparatus for which a central image axis of the radioscopic imaging unit is aligned with a desired trajectory previously identified in the target;

a positioning means adapted to move the radioscopic imaging apparatus to align a central image axis of the video imaging device with the desired trajectory; and a monitor for showing a live video feed of the surgical procedure with a radioscopic image overlaid over the live video feed for tracking a position of a surgical object relative to the desired trajectory.

9. The intraoperative navigation system according to claim 8, comprising a position control unit adapted to generate motion parameters for the positioning means.

10. The intraoperative navigation system according to claim 9, wherein the radioscopic imaging arrangement comprises a radiation source and a radiation detector.

11. The intraoperative navigation system according to claim 8, wherein the radioscopic imaging arrangement comprises a radiation source and a radiation detector.

12. The intraoperative navigation system according to claim 8, wherein the video imaging device is arranged on the radioscopic imaging apparatus at a fixed position relative to the detector.

13. The intraoperative navigation system according to claim 8, comprising an image processing unit adapted to receive video data from the video imaging device.

14. The intraoperative navigation system according to claim 13, wherein the image processing unit is adapted to determine a trajectory point in the live video feed that corresponds to an intersection of the desired trajectory with a video image plane.

15. The intraoperative navigation system according to claim 13, wherein the image processing unit is adapted to overlay a visual alignment aid in the live video feed.

16. The intraoperative navigation system according to claim 13, wherein the image processing unit is adapted to center the visual alignment aid about the trajectory point in the live video feed.

17. The intraoperative navigation system according to claim 13, wherein the image processing unit is adapted to determine a degree of alignment between a surgical implement and the desired trajectory.

18. The intraoperative navigation system according to claim 9, wherein the image processing unit is adapted to overlay a radioscopic image over the live video feed.

19. The intraoperative navigation system according to claim 9, wherein the image processing unit is adapted to overlay the desired trajectory on a radioscopic image obtained during the surgical procedure.

20. A computer program product comprising a computer program stored on a non-transitory computer-readable medium that is directly loadable into a memory of a control unit of an intraoperative navigation system and which comprises program elements for performing steps of the method according to claim 1 when the computer program is executed by the control unit of the intraoperative navigation system.

21. A non-transitory computer-readable medium on which are stored program elements that can be read and executed by a computer unit in order to perform steps of the method according to claim 1 when the program elements are executed by the computer unit.

* * * * *